United States Patent
De Mesanstourne et al.

(10) Patent No.: US 6,335,370 B1
(45) Date of Patent: Jan. 1, 2002

(54) FLUID CONCENTRATED HYDROALCOHOLIC COMPOSITIONS OF COPRA OR OIL PALM ALKYL-AMIDOPROPYLBETAINS

(75) Inventors: Regine De Mesanstourne, Maisons-Lafitte; Stephane Fouquay, Mont-Saint-Avignan; Jean-Paul Gamet, Savy-Berlette; Francois Guillemet, Paris, all of (FR)

(73) Assignee: Ceca S.A., Puteaux (FR)

( * ) Notice: Subject to any disclaimer, the term of this patent is extended or adjusted under 35 U.S.C. 154(b) by 0 days.

(21) Appl. No.: 09/331,974
(22) PCT Filed: Oct. 27, 1998
(86) PCT No.: PCT/FR98/02297
§ 371 Date: Feb. 2, 2000
§ 102(e) Date: Feb. 2, 2000
(87) PCT Pub. No.: WO99/24157
PCT Pub. Date: May 20, 1999

(30) Foreign Application Priority Data

Nov. 7, 1997 (FR) .............................................. 97 14034

(51) Int. Cl.$^7$ ................................................. A61K 31/14
(52) U.S. Cl. ........................... 514/642; 554/52; 554/68; 554/69
(58) Field of Search ........................... 514/642; 551/52, 551/68, 69

(56) References Cited

U.S. PATENT DOCUMENTS 4,832,871 A * 5/1989 Bade .......................... 252/546

FOREIGN PATENT DOCUMENTS

EP 243619 11/1987

* cited by examiner

Primary Examiner—Dwayne C. Jones
(74) Attorney, Agent, or Firm—Millen, White, Zelano & Branigan, P.C.

(57) ABSTRACT

Aqueous-alcoholic solutions of coconut or palm oil alkyla-midopropylbetaines with a betaine content of greater than 50%, which are fluid, stable and pumpable are described as occupying a well-defined zone of their betaine/water/ethanol ternary diagram. They are prepared by synthesis and quaternization of the amidoamine directly in the solvent medium in which they are defined.

10 Claims, No Drawings

FLUID CONCENTRATED HYDROALCOHOLIC COMPOSITIONS OF COPRA OR OIL PALM ALKYL-AMIDOPROPYLBETAINS

This application is a 371 of PCT/FR98/02297, filed on Oct. 27, 1998.

The invention relates to concentrated, aqueous-alcoholic, low-viscosity, clear, relatively colourless solutions which are stable over a temperature range of between 5 and 50° C. and which contain at least 50% by weight of alkylamidopropylbetaine corresponding to the general formula (I):

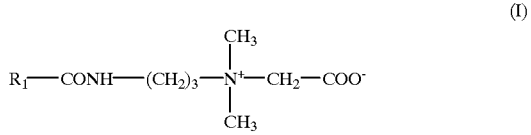

in which $R_1$ represents the alkyl radical of a natural fraction of fatty acids of coconut or palm oil type, which are, approximately, saturated fatty acids with about 40–50% of lauric acid and 15–20% of myristic acid (in the account hereinbelow this will be referred to simply as betaine). The solutions have these qualities only if their composition is chosen precisely in a region of the betaine/ethanol/water diagram standardized to 100 on a weight basis after correction of the NaCl present.

Betaines corresponding to the general formula (I) are amphoteric surfactants that are very well tolerated by the skin, they have excellent cleansing and foaming properties and are entirely suitable for making a whole range of surfactant compositions, such as washing agents, cleansing agents (liquid products for washing up by hand), haircare compositions (shampoos) and bodycare compositions (shower gels and bubble baths).

The preparation of this type of betaine is described in many documents, and the processes are known to those skilled in the art, for example U.S. Pat. No. 3,225,074 (American Cyanamid). It consists in reacting a fatty acid or a fatty acid fraction with N,N-dimethyl-1,3-propanediamine (DMAPA) between 140 and 200° C., and then in quaternizing the tertiary amidoamine obtained, of general formula (II):

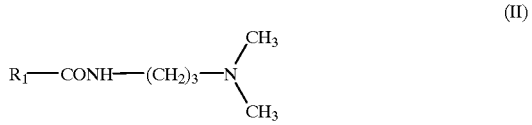

with monochloroacetic acid in the presence of an alkaline salt or the corresponding salt of this acid, the quaternization reaction usually taking place in aqueous medium. The alkaline chloride, which is often sodium chloride, obtained as a by-product in the reaction, is generally left in this aqueous betaine solution. These aqueous betaines are sold at a concentration in the region of 30% by weight.

Attempts have often been made to prepare industrially betaine solutions that are as concentrated and as fluid as possible, for quite understandable reasons of reducing the transportation and storage costs, without, however, sacrificing the ease of their handling.

A person skilled in the art knows that when the concentration of an aqueous surfactant solution increases, its viscosity also increases. Nevertheless, certain authors have sought to concentrate, by evaporation under reduced pressure, betaine solutions obtained according to the usual processes, but their viscosity increases rapidly and they become pasty at about 40° C. by weight of betaine, then continue to solidify as water is removed therefrom; it is not possible to obtain concentrated solutions via this route. However, it is reported in EP 0,302,329 (Th. Goldschmidt) that it was possible partially to circumvent this difficulty by adjusting the pH of the solution to between 1 and 4.5 with an inorganic acid (hydrochloric, sulphuric or phosphoric acid). The authors thus obtained solutions containing 43 to 44% by weight of betaine (or 53 to 54% solids) with a viscosity in the region of 1000 mPa.s at 25° C. However, the problems of corrosion during storage and transportation, along with the atypical pH of these betaine solutions, limit their use and, moreover, they gel below 16° C.

Another route is that for obtaining betaine in powder form, by spraying fluid solutions at less than 30%. It may be thought to redissolve these powders in suitable solvents, but redissolving these powders is hampered by the formation, when the powder is placed in contact with the solvent, of lumps or gelled pastes which are virtually impossible to redissolve, or at least not within reasonable times that are compatible with industrial activity.

International patent application WO 95/12856 (Henkel) discloses and claims a process for manufacturing surfactants of betaine type with a low salt content (0.98 to 1.01% residual NaCl) by quaternization of tertiary amines and/or tertiary amidoamines with sodium monochloroacetate in an aqueous-alcoholic mixture composed of 5 to 10% by weight of water and 35 to 50% by weight of ethanol and/or isopropanol, this reaction being followed by removal of the salt fraction precipitated, total removal of the solvent and readjustment of the water in the reaction medium in order to bring the solution to the desired active material concentration —in this case 30%. The water/ethanol weight ratio claimed by the authors is typical for a process aimed at removing the NaCl formed during the reaction. A composition of this type formed the subject of U.S. Pat. No. 4,705,893 (KAO), represented by a pentagonal zone of the betaine/water/ethanol ternary diagram defined by the triangular coordinates (80/10/10), (80/15/5), (40/55/5), (40/27.5/32.5) and (52.5/10/37.5). Both of these cases involve processes whose essential aim is to obtain totally aqueous non-concentrated amphoteric surfactant solutions with low salt contents.

A person skilled in the art is familiar with the idea of the possible existence of domains of fluid phases in an amphoteric surfactant/water/solvent system. This idea is pursued in WO 95/14076 (Albright and Wilson), in reality without any concrete teaching other than that of the individual examples reported in that publication, which come closest to the conditions of the present problem, namely, compositions of cocoor lauryl-amidopropylbetaine—salt dissolved in a mixed solvent of water/glycol type.

The problem which still remains is to obtain solutions of coconut or palm oil alkylbetaine which are as concentrated as possible, i.e. at least 50% by weight, clear and relatively colourless, fluid and pumpable (viscosity of less than 1000 mPa.s), stable between 5 and 50° C. for prolonged periods, in order to reduce the packaging, transportation and storage costs, readily manipulable, and which can be formulated in their given state with other surfactants, for example alkyl ether sulphates, alkanolamides or other starting materials forming part, in particular, of the formulations for liquid soaps, shampoos, shower gels and other cosmetic preparations.

The present invention provides a solution to this technical problem, which consists in preparing the alkylbetaine in the presence of small amounts of ethanol, provided that, however, the system remains limited to a quite precise and narrow region of the phase diagram as will now be defined.

The reckoning is determined on betaine/water/ethanol ternary compositions, represented on the ternary diagram in reduced coordinates $B^* = [\text{betaine}/(\text{betaine}+\text{water}+\text{ethanol})] \cdot 10^2$ $W^* = [\text{water}/(\text{betaine}+\text{water}+\text{ethanol})] \cdot 10^2$ $E^* = [\text{ethanol}/(\text{betaine}+\text{water}+\text{ethanol})] \cdot 10^2$ where betaine has the sense of, and is measured as, betaine=solids−NaCl, in which the 100% loop relationship applies for the composition $B^*+W^*+E^*=100$, all of the betaine, solids, water, ethanol and NaCl magnitudes being expressed on a weight basis, the reduced magnitudes $B^*$, $W^*$ and $E^*$ appearing as weight %.

With this definition, the betaine considered is a raw betaine, i.e. one consisting of alkylamidobetaine as corresponds to formula I, with a few reactant residues and a few reaction by-products not exceeding 3% by weight (see Example 1).

The compositions of the invention are those which obey the following relationships $55\% \leq B^* \leq 62\%$ $E^* \geq 21\%$ $37\% \leq W^*/W^*+E^* \leq 50\%$ In the compositions of the invention, NaCl is present to a maximum level of 4.5% by weight, beyond which value these compositions become uncontrollable, if only by precipitation of the salt.

The compositions according to the invention are capable of prolonged storage over periods of at least three months, in the course of which no gelling, demixing, precipitation of salts or appreciable change in colour or clarity is observed in the temperature range between 5 and 50° C. These solutions also have the advantage of being relatively non-foaming in the concentrated state, which makes them easier to manipulate. Another advantage lies in the fact that these concentrated solutions are sufficiently resistant to microbial invasion, such that it is unnecessary to add preserving agents. These characteristics make these solutions particularly suitable for making cosmetic compositions.

Another subject of the present invention relates to the process for manufacturing these concentrated solutions, which consists in preparing the intermediate coconut or palm oil dimethylamidopropylamides and in quaternizing them with monochloroacetic acid in the presence of sodium hydroxide or sodium monochloroacetate directly in the solvent medium chosen, i.e. obeying the composition rule $E^* \geq 21\%$ $37\% \leq W^*/W^*+E^* \leq 50\%$ defined above.

The examples and counterexamples which follow will allow a better understanding of the invention to be gained.

EXAMPLE 1

Manufacture of a coconut betaine containing about 59.2% by weight of betaine, i.e. 63.3% solids, whose reduced coordinates $B^*/W^*/E^*$ in the phase diagram are 61.7/15.4/22.9 (in weight %).

1/a—Preparation of The Coconut Amidoamine (Mw=208 g)

731 kg of coconut fatty acid, melted at 50° C., are loaded in a reactor. The reactor and its contents are bubbled with nitrogen and brought to 190° C. 366 kg of dimethylaminopropylamine (DMAPA) are added over 4 hours via a dip tube, the distillation waters being removed continuously. The mixture is maintained at 190° C. under a stream of nitrogen until the reaction product shows an acid number of less than 4.5 mg KOH/g. The mixture is cooled to 150° C., 100 kg of water are injected, via a dip tube, over 1 hour and the resulting mixture is dried at 150° C. while bubbling nitrogen through, to a water content of less than 0.1%. The system is cooled to 60° C., the bubbling of nitrogen is stopped and the reactor is emptied.

The usual characteristics of the tertiary amidoamine thus obtained are as follows:

| | |
|---|---|
| $HClO_4$ alkalinity | 3.40–3.45 meq/g |
| IA | 4.4 mg KOH/g |
| Free fatty acid | 1.6% |
| Free DMAPA | 57 ppm |
| Water content | <0.1% |
| Solidification point | 21° C. |
| Flow point | 24° C. |

1/b—Manufacture of the Concentrated Coconut Betaine Solution 197 kg of ethanol are loaded into another reactor at room temperature, followed by 169 kg of monochloroacetic acid. The mixture is brought to 25° C. and 473 kg of the amidoamine prepared in 1/a are then added slowly, while controlling the exothermicity so that the temperature does not exceed 40° C. 159 kg of 50% sodium hydroxide are then added over about one hour, while maintaining the temperature at 40° C., after which it is raised slowly to 80° C. The mixture is maintained at this temperature until the amidoamine content reaches a stable value of 1%, taking care to ensure that the pH of a test sample prediluted to 5% in water is still between 10–10.5. After one hour, the mixture is cooled to 40° C. and the pH is adjusted to 6.5 with 31% HCl solution. The NaCl fraction precipitated is removed by decantation, filtration or centrifugation.

A concentrated betaine solution having the following main compositions is thus obtained:

| | Weight values | | Reduced coordinates[c] |
|---|---|---|---|
| Solids[a] | 63.3% | | |
| NaCl | 4.1% | | |
| Betaine[b] | 59.2% | $B^*$ | 61.7%[c] |
| Water | 14.8% | $W^*$ | 15.4%[c] |
| Ethanol | 21.9% | $E^*$ | 22.9%[c] |

[a]: 20 minutes at 105° C.
[b]: Betaine active material = solid-NaCl (including glycolate, free fatty acid and free amidoamine)
[c]: $B^*$, $W^*$ and $E^*$ values in the ternary diagram, after correcting the NaCl content and then normalizing to 100 by weight and the following associated characteristics:

| | |
|---|---|
| Sodium monochloroacetate | <5 ppm |
| Free DMAPA | <5 ppm |
| Sodium glycolate | 0.3% |
| Free fatty acid | 0.8% |
| Free amidoamine | 1.0% |
| pH at 5% (23° C.) | 6.5 |
| Brookfield viscosity at 5° C.[d] | 555 mPa.s |
| Brookfield viscosity at 23° C.[d] | 171 mPa.s |

-continued

| | |
|---|---|
| Brookfield viscosity at 45° C.[d] | 68 mPa.s |
| Hazen colour (t = 0) | 100 Hz |
| Hazen colour (t = 6 weeks)[e] | 110 Hz |

[d]Rheomat 180: spindle 12; speed 231 (5° C.)/354 (23° C.)/1291 (45° C.)
[e]Maturation at 45° C.

This is a fluid, clear, easily pumpable solution which is stable between 5 and 50° C.

COUNTEREXAMPLE 1

The operating conditions of step 1/b of Example 1 are repeated, except for the loads of starting materials, which were adjusted to obtain a coconut betaine at approximately 66.2% betaine, i.e. 68.7% solids, for which the corrected triangular coordinates B*/W*/E* of NaCl in the phase diagram are 67.8/14.1/18.1 (in weight %).

A viscous, non-newtonian, birefringent gel of liquid crystal type which is difficult to manipulate and to formulate between 5 and 50° C. is obtained.

COUNTEREXAMPLE 2

The operating conditions of step 1/b of Example 1 are repeated, except for the loads of starting materials, which were adjusted to obtain a coconut betaine at approximately 62.6% raw betaine, i.e., 65.0% solids, for which the corrected triangular coordinates B*/W*/E* of NaCl in the phase diagram are 64.1/15.4/20.5 (in weight %).

A fluid, clear solution which is a single phase in the region of room temperature (20–25° C.) but which, between 5 and 15° C., undergoes a rapid change to a two-phase mixture with a birefringent viscous gel phase and a supernatant liquid phase. This heterogeneous product is difficult to use in this state.

COUNTEREXAMPLE 3

The same operating conditions as in step 1/b of Example 1 are repeated, except for the loads of starting materials, which were adjusted to obtain a coconut betaine at approximately 57.5% betaine, i.e. 61.6% solids, for which the corrected triangular coordinates B*/W*/E* of NaCl in the phase diagram are 60/25/15 (in weight %).

A viscous, non-newtonian, birefringent gel of liquid crystal type which is difficult to manipulate and to formulate between 5 and 50° C. is obtained.

COUNTEREXAMPLE 4

The operating conditions of step 1/b of Example 1 are repeated, except for the loads of starting materials, which were adjusted to obtain a coconut betaine at approximately 47.8% betaine, i.e. 52.3% solids, for which the corrected triangular coordinates B*/w*/E* of NaCl in the phase diagram are 50/35/15 (in weight %).

A viscous, non-newtonian, birefringent gel of liquid crystal type which is difficult to manipulate and to formulate between 5 and 50° C. is obtained.

COUNTEREXAMPLE 5

The same operating conditions as in step 1/b of Example 1 are repeated, except for the loads of starting materials, which were adjusted to obtain a coconut betaine at approximately 58.2% betaine, i.e. 60% solids, for which the corrected triangular coordinates B*/W*/E* of NaCl in the phase diagram are 58.5/13.5/28.0 (in weight %).

A solution which becomes heterogeneous on storage at 5° C. is obtained.

We claim:

1. Compositions containing an alkylamidopropylbetaine, salt, water and ethanol, in the form of fluid solutions that are easy to pump, clear, relatively colourless, stable between 5 and 50° C. and have a viscosity of less than 1000 mPa.s, the alkyl radical of the said alkylamidopropylbetaine being that of a natural fraction of fatty acid of coconut or palm oil type, characterized in that the betaine, water and ethanol components, given as reduced compositions by $B^* = [\text{betaine}/(\text{betaine}+\text{water}+\text{ethanol})] \cdot 10^2$ $W^* = [\text{water}/(\text{betaine}+\text{water}+\text{ethanol})] \cdot 10^2$ $E^* = [\text{ethanol}/(\text{betaine}+\text{water}+\text{ethanol})] \cdot 10^2$ where betaine has the sense of, and is measured as, betaine= solids−NaCl,
are linked by the relationships $55\% \leq B^* \leq 62\%$ $E^* \geq 21\%$ $37\% \leq W^*/W^* + E^* \leq 50\%$ which define their field of existence of the compositions as long as their salt content is less than 4.5% by weight.

2. Process for obtaining compositions as described in claim 1, which consists in preparing intermediate coconut or palm oil dimethylamidopropylamides and in quaternizing them with monochloroacetic acid in the presence of sodium hydroxide or with sodium monochloroacetate directly in the water/ethanol solvent medium composed so as to give $E^* \geq 21\%$ $37\% \leq W^*/W^* + E^* \leq 50\%$ the reduced compositions E* and W* having the meanings given in claim 1.

3. A composition according to claim 1, consisting essentially of said alkylamidopropylbetaine, salt, water and ethanol.

4. A composition according to claim 1, wherein said ethanol is the sole alcoholic component in the composition.

5. In the preparation of a formulation of a liquid soap, shampoo, shower gel or cosmetic preparation, the improvement comprising adding to said formulation a composition according to claim 1.

6. In the preparation of a formulation of a liquid soap, shampoo, shower gel or cosmetic preparation, the improvement comprising adding to said formulation a composition according to claim 3.

7. In the preparation of a formulation of a liquid soap, shampoo, shower gel or cosmetic preparation, the improvement comprising adding to said formulation a composition according to claim 4.

8. A formulation prepared in accordance with the process of claim 6.

9. A formulation prepared in accordance with the process of claim 7.

10. A formulation prepared in accordance with the process of claim 8.

* * * * *